US00PP33452P3

(12) United States Plant Patent
van Geest

(10) Patent No.: US PP33,452 P3
(45) Date of Patent: Sep. 7, 2021

(54) ***FICUS* PLANT NAMED 'ESPE1902'**

(50) Latin Name: *Ficus benghalensis*
Varietal Denomination: ESPE1902

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 17/092,243

(22) Filed: Nov. 7, 2020

(65) Prior Publication Data

US 2021/0161046 P1 May 27, 2021

(51) Int. Cl.
*A01H 5/12* (2018.01)
*A01H 6/00* (2018.01)
*A01H 5/08* (2018.01)

(52) U.S. Cl.
USPC ..... Plt./211
CPC ..... *A01H 6/00* (2018.05); *A01H 5/08* (2013.01)

(58) Field of Classification Search
USPC ..... Plt./211, 373
See application file for complete search history.

*Primary Examiner* — Susan McCormick Ewoldt
(74) *Attorney, Agent, or Firm* — Samuel R. McCoy, Jr.

(57) ABSTRACT

A new and distinct variety of *Ficus* plant named 'ESPE1902' which is characterized by the combination of a compact growth habit, small pubescent leaves borne on pubescent petioles, pubescent lateral branches, and the stability of all characteristics from generation to generation.

2 Drawing Sheets

Latin name of the genus and species: The Latin name of the genus and species of the novel variety disclosed herein is *Ficus benghalensis.*

Variety denomination: The inventive variety of *Ficus* disclosed herein has been given the variety denomination 'ESPE1902'.

CROSS REFERENCE TO RELATED APPLICATIONS

This application claims priority to the Community Plant Variety Rights application number 2019/3117, Nov. 27, 2019, which is herein incorporated by reference.

BACKGROUND OF THE INVENTION

Parentage: 'ESPE1902' originated as a naturally occurring, whole-plant mutation of an unnamed *Ficus benghalensis* plant (not patented). In the summer of 2014, the inventor discovered the mutation at his commercial greenhouse in 's-Gravenzande, the Netherlands, growing amongst a cultivated population of *Ficus benghalensis* plants. The mutation was noted for its compact habit and small foliage and was subsequently isolated for further evaluation in order to confirm the distinctness and stability of the characteristics first observed. Upon confirmation of distinctness and stability, 'ESPE1902' was selected for commercialization.

Asexual Reproduction: Asexual reproduction of 'ESPE1902', by way of stem cuttings, was first initiated in September of 2014 at a commercial greenhouse in 's-Gravenzande, the Netherlands. Through five subsequent generations, the unique features of this cultivar have proven to be stable and true to type.

SUMMARY OF THE INVENTION

The cultivar 'ESPE1902' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'ESPE1902'. These characteristics in combination distinguish 'ESPE1902' as a new and distinct *Ficus* cultivar:

1. *Ficus* 'ESPE1902' exhibits a compact growth habit; and
2. *Ficus* 'ESPE1902' exhibits relatively small foliage; and
3. *Ficus* 'ESPE1902' exhibits pubescent lateral branches, petioles, and foliage.

BOTANICAL DESCRIPTION OF THE PLANT

Figure 1:
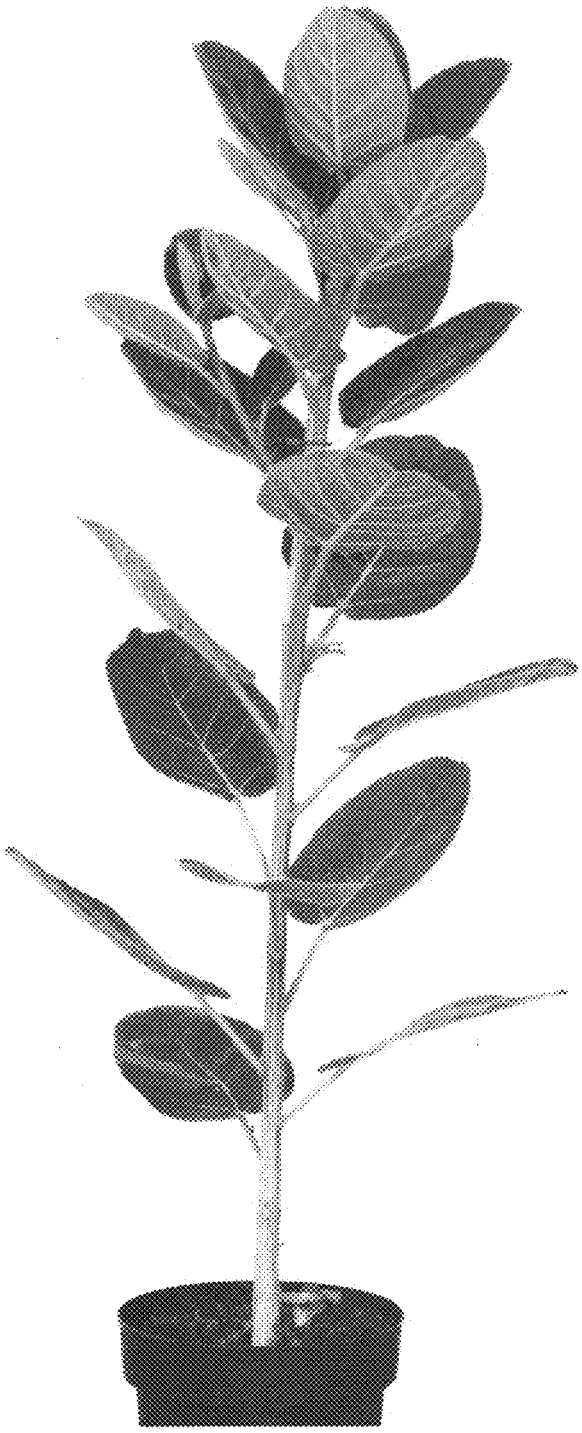
FIG. 1 illustrates, as nearly true as it is reasonably possible to make the same in color photographs of this type, an exemplary plant of 'ESPE1902' grown in a commercial greenhouse in 's-Gravenzande, the Netherlands. This plant is approximately 25 weeks old, shown planted in a 19 cm container.
Figure 2:
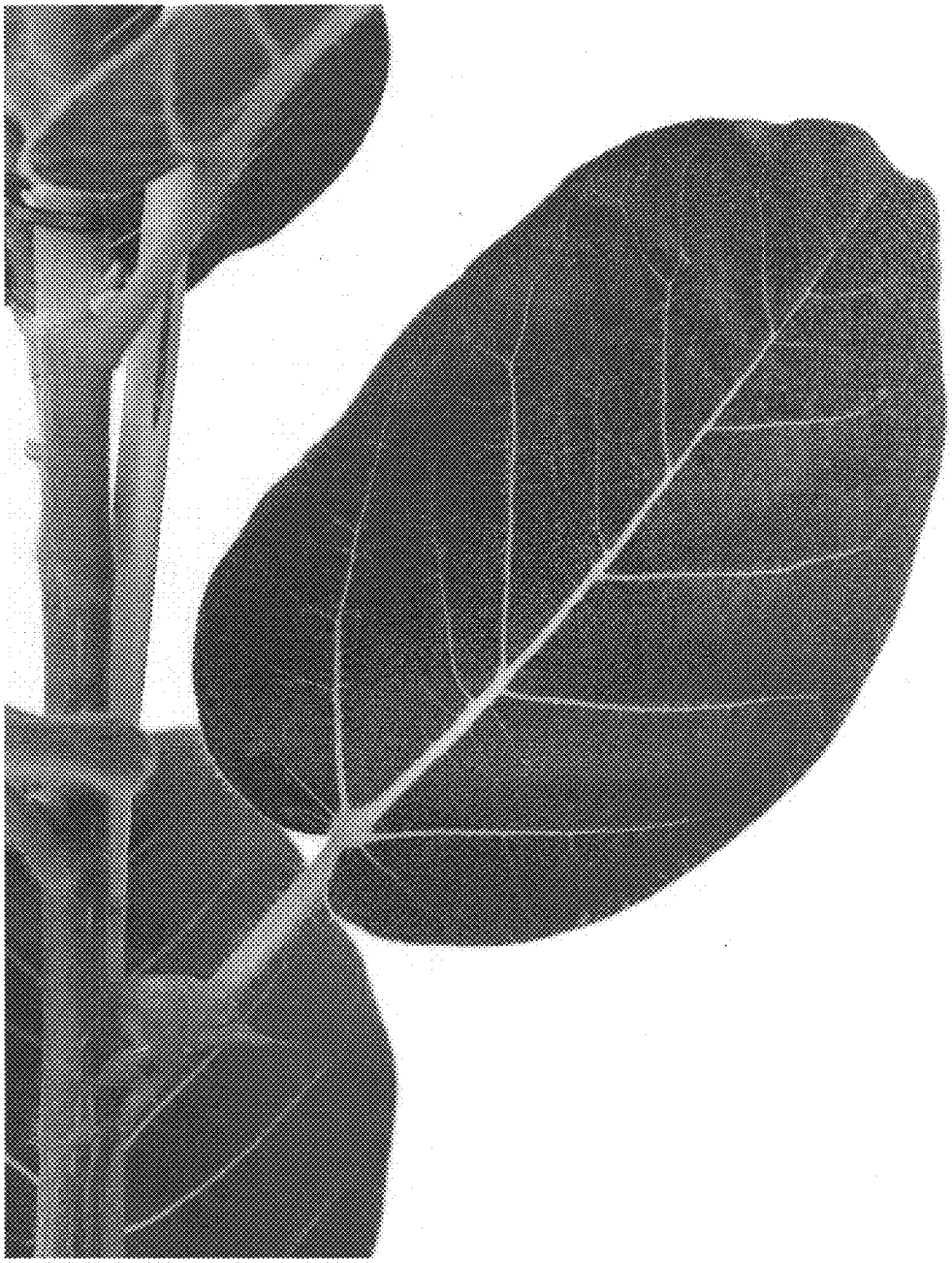
FIG. 2 illustrates, as nearly true as it is reasonably possible to make the same in color photographs of this type, the mature foliage of 'ESPE1902'.

The following observations and measurements were made in August of 2020 and describe a sample set of six 25 week-old 'ESPE1902' plants grown in 19 cm nursery pots, at a greenhouse in 's-Gravenzande, the Netherlands. Plants were produced in a greenhouse with full sun exposure, ebb and flood irrigation tables, no supplemental fertilizer, and no preventative or pest control measures utilized.

Those skilled in the art will appreciate that certain characteristics will vary with older or, conversely, with younger plants. 'ESPE1902' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'ESPE1902' and comparisons with the parent plant and most similar commercial variety of *Ficus* are provided below.

Plant description:

*Growth habit*.—Upright.

*Plant form*.—Oblong.

*Average height*.—97.2 cm from the soil level to the top of the foliar plane.

*Plant spread*.—Average of 40.5 cm.

*Growth rate*.—Moderately fast to fast.

*Plant vigor*.—Vigorous.

*Propagation type*.—Stem cuttings.

*Time to produce a rooted cutting*.—Approximately 40 days to produce a rooted cutting at approximately 25 degrees Celsius.

*Time to produce a finished plant*.—Approximately 18 weeks to produce a marketable finished plant in a 17 cm pot.

*Disease and pest resistance*.—Neither resistance nor susceptibility to typical *Ficus benghalensis* pests and diseases has been observed.

*Environmental tolerances*.—Adapt to, at least, USDA Zones 10 through 13 and temperatures as high as 40 degrees Celsius; moderate to high tolerance to rain; low to moderate tolerance to wind.

Root system:

*General*.—Moderately dense, moderately branched rooting; roots are fibrous.

*Distribution in the soil profile*.—Moderately deep.

*Diameter of roots*.—1.5 mm on average.

*Texture*.—Smooth; no root hairs.

*Color*.—Greyed-yellow, nearest to a mixture of RHS 162B and 162C.

Stems and branches:

*General branching habit*.—One main stem; with sparse lateral branching. Pinching isn't required but will improve branching.

*Main stem*.—Length — Approximately 86.2 cm. Diameter — Approximately 1.3 cm. Internode length — Approximately 4.8 cm. Attitude — Near vertical. Aspect — Rounded. Strength — Strong. Texture — Juvenile stems are densely covered with thin hairs with an average length of 0.3 cm. Hairs are colored greyed-yellow, nearest to RHS 161 D. Mature stems are glabrous. Color, juvenile — Yellow-green, nearest to RHS 144A. Color, mature — Yellow-green, nearest to RHS 146B and axially striped greyed-orange, nearest to a mixture of RHS 1648 and 164C. Color at the leaf nodes — Yellow-green, nearest to RHS 146B. Color of the oldest wood — Greyed-green, nearest to a mixture of RHS 198B and 198C, and axially striped greyed-orange, nearest to RHS 164A.

*Lateral branches*.—Quantity of lateral branches — 2. Attitude — Outward. Aspect — Rounded. Strength — Strong. Texture — Densely covered with thin hairs with an average length of 0.3 cm. Hairs are colored greyed-yellow, nearest to RHS 161D. Color, juvenile — Yellow-green, nearest to RHS 144A. Color, mature — Yellow-green, nearest to RHS 146B and axially striped greyed-orange, nearest to a mixture of RHS 164B and 164C. Color at internodes — Yellow-green, nearest to RHS 146B.

Foliage:

*Arrangement*.—Alternate.

*Division*.—Simple.

*Quantity*.—19 leaves per main stem.

*Attitude*.—Upward and outward.

*Lamina*.—Shape — Long cordate to broad ovate. Aspect — Flat to slightly concave. Dimensions — 18.0 cm long and 13.8 cm wide. Apex — Undeeply retuse. Base — Cordate. Margin — Entire; slightly, coarsely repand. Texture of the adaxial surface — Slightly rugose and densely hirsute; hairs are colored greyed-white, nearest to RHS 156D, with an average length of 0.2 mm. Texture of the abaxial surface — Moderately rugose and hirsute, particularly along the veins; hairs are colored greyed-yellow, nearest to RHS 160D, with an average length of 0.2 mm. Luster of the adaxial surface — Slightly glossy. Luster of the abaxial surface — Very slightly glossy. Color — Juvenile foliage, adaxial surface — Green, nearest to RHS NN137B, and veined yellow-green, nearest to RHS 144B. Juvenile foliage, abaxial surface — Yellow-green, nearest to RHS 147B, and veined lighter, nearest to RHS 145A. Mature foliage, adaxial surface — Nearest to in between yellow-green and greyed-green, RHS 147A and N189A yet darker. Mature foliage, abaxial surface — Yellow-green, nearest to RHS 147B. Venation — Pattern — Pinnate, reticulate. Color, adaxial surface — Yellow-green, nearest to in between RHS N145C and 150D. Color, abaxial surface — Yellow-green, nearest to in between RHS N145D and 150D. Petiole — Length — 7.3 cm. Diameter — 0.6 cm. Strength — Strong. Texture — Densely hirsute; hairs are colored greyed-yellow, nearest to RHS 160D, with an average length of 0.2 mm. Luster — Matte to very slightly glossy. Color, adaxial surface — Yellow-green, nearest to RHS 144B. Color, abaxial surface — Yellow-green, nearest to a mixture of RHS 144B and 144C. Stipule — General — A single dry stipule is present at the base of each leaf. Shape — Ovate. Length — 3.9 cm. Diameter — 2.7 cm. Aspect — Concave. Apex — Acute to emarginated. Base — Broad cuneate. Margin — Entire; undulate. Texture, adaxial — Smooth; glabrous. Texture, abaxial — Moderately hirsute; hairs colored greyed-yellow, nearest to RHS 160D, with an average length of 0.3 mm. Luster Matte. Color, adaxial surface — Greyed-orange, nearest to a mixture of RHS 164A, 164B, 164C, and 164D. Color, abaxial surface — Greyed-orange, nearest to a mixture of RHS 164B, 165B, and 165C.

Inflorescence: No flowering has been observed to date.

COMPARISON WITH THE PARENT PLANT

Plants of the new cultivar 'ESPE1902' differ from the parent, an unnamed *Ficus benghalensis* plant (not patented), in the following characteristics described in Table 1 below.

TABLE 1

| Characteristic | 'ESPE1902' | The parent |
|---|---|---|
| Growth habit. | More compact than the parent. | Less compact than 'ESPE1902'. |
| Foliage size. | Smaller than the parent. | Larger than 'ESPE1902' |
| Lateral branch pubescence. | Pubescent. | Glabrous. |
| Petiole and foliage pubescence. | Pubescent. | Glabrous. |

COMPARISON WITH THE CLOSEST KNOWN COMPARATOR

Plants of the new cultivar 'ESPE1902' differs from the variety, *Ficus benghalensis* 'Audrel' (Community Plant Variety Rights grant number 15321), in the following characteristics described in Table 2 below.

TABLE 2

| Characteristic | 'ESPE1902' | 'Audrel' |
|---|---|---|
| Growth habit. | More compact than 'Audrel'. | Less compact than 'ESPE1902'. |
| Foliage luster. | Slightly glossy; less glossy when compared to 'Audrel'. | Glossier than 'EPSE1902'. |
| General coloration of the oldest wood of the main stem. | More brown compared to 'Audrel'. | Less brown compared to 'Audrel'. |
| Foliage shape. | More ovate. Long cordate to broad ovate. | Elliptic. |
| Foliage margin undulation. | Coarsely undulated. | Slightly angulate; moderately undulate. |

That which is claimed is:

1. A new and distinct variety of *Ficus* plant named 'ESPE1902', substantially as described and illustrated herein.

* * * * *